United States Patent [19]

Mascoli et al.

[11] 4,292,405
[45] Sep. 29, 1981

[54] STERILITY TEST SET

[75] Inventors: Carmine C. Mascoli, Deerfield; J. Lee Pope, Jr., Antioch; Phillip L. Weber, Niles, all of Ill.

[73] Assignee: Baxter Travenol Laboratories, Inc., Deerfield, Ill.

[21] Appl. No.: 122,548

[22] Filed: Feb. 19, 1980

Related U.S. Application Data

[63] Continuation of Ser. No. 885,747, Mar. 13, 1978.

[51] Int. Cl.$^3$ ............................ C12Q 1/22; C12M 1/12
[52] U.S. Cl. ........................................ 435/31; 435/311
[58] Field of Search ................... 435/31, 34, 292, 296, 435/299, 311, 313, 803; 23/230 B; 422/68, 69, 74, 103; 210/203, 340, 341

[56] References Cited

U.S. PATENT DOCUMENTS 4,036,698 7/1977 Bush et al. ........................ 435/34 X Primary Examiner—Robert J. Warden
Attorney, Agent, or Firm—Paul C. Flattery; Lawrence W. Flynn; Max D. Hensley

[57] ABSTRACT

A system is provided for testing the sterility of a plurality of samples. The samples are fed by gravity to and through a first conduit which branches into a pair of conduits terminating in two separate test chambers. Each of the test chambers has a main chamber portion and a filter therein. The sample material is gravity fed into the main chamber portions and a vacuum pump is used to draw the liquid material through the filter and out of the test chamber. Test media is introduced to each of the test chambers through an injection site and the test chambers are incubated.

3 Claims, 6 Drawing Figures

U.S. Patent  Sep. 29, 1981  Sheet 3 of 3  4,292,405
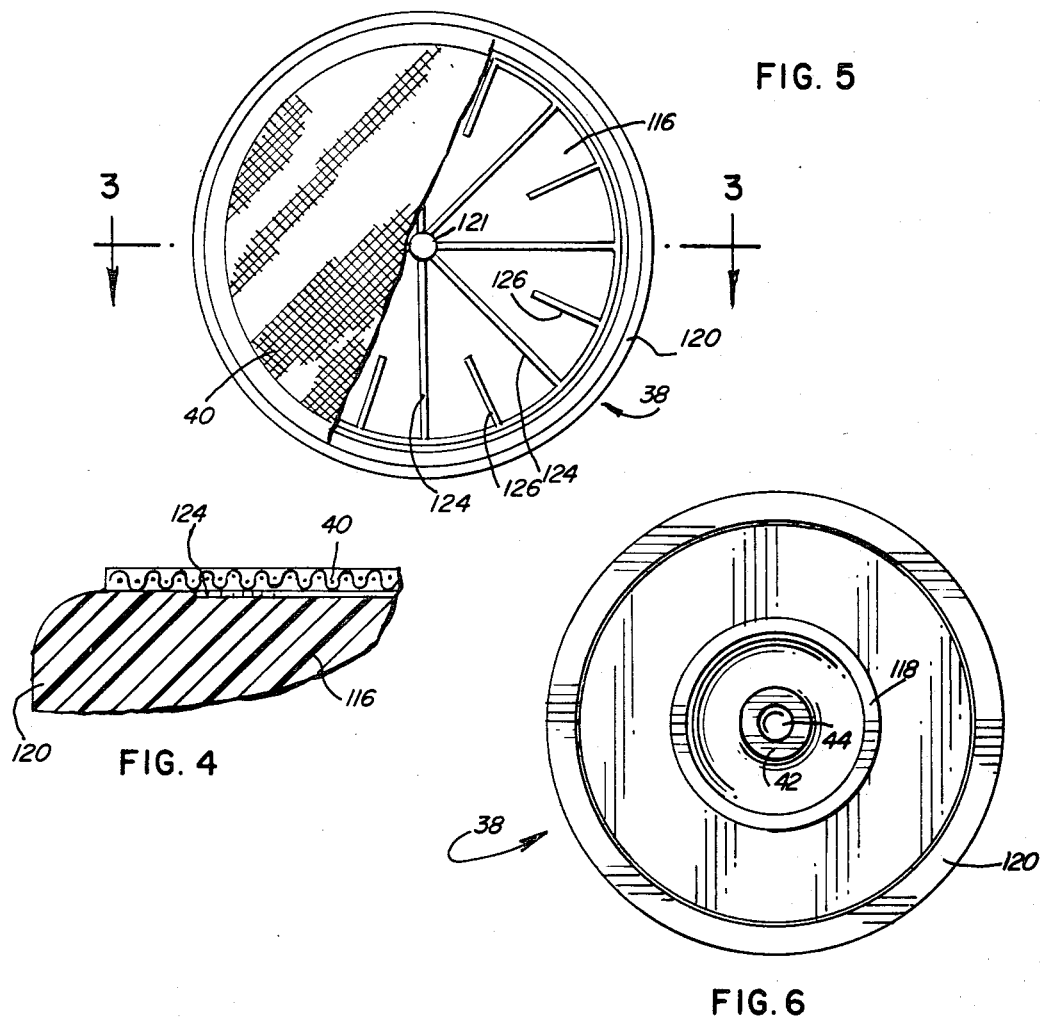
FIG. 5
FIG. 4
FIG. 6
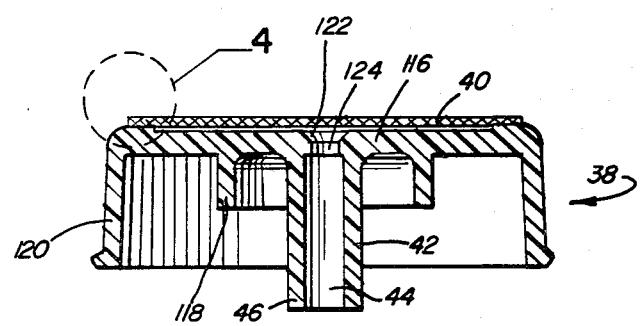
FIG. 3

STERILITY TEST SET

This application is a continuation of U.S. patent application Ser. No. 885,747, filed Mar. 13, 1978 and entitled "Sterility Test Set".

BACKGROUND OF THE INVENTION

The present invention concerns a system for testing a sample or samples for sterility and, more particularly, a sterility test system which significantly alleviates problems of extraneous contamination.

Many systems are available in the prior art for the testing of sterility by using a membrane filter method. In one prior art system, during production of bottles of a sterile liquid or medicament, after sterilization a number of bottles are taken at random and are dispensed into a single filter unit. After the solution has been received within the filter unit, the filter is removed and cut in half. One of the halves is introduced to a test medium that is conductive to growth of bacteria and the other half is introduced to another test medium which is conducive to the growth of mold. The filter halves are incubated and respectively inspected for bacteria and mold.

A disadvantage of the aforementioned prior art sterilization test is the necessity of opening the filter unit and cutting the filter, which steps are conducive to contamination. Another type of prior art sterilization testing system, for testing one sample at a time, is disclosed in U.S. Pat. No. 4,036,698. In this system, the liquid sample is drawn by a vacuum pump through a pair of filter canisters, thereafter the air is removed from each of the filter canisters, test media are introduced to each of the canisters and the canisters are incubated. The patent states that an alternative to using the vacuum pumping is to replace the vacuum pump with a peristaltic action pump.

The use of peristaltic pumps to feed the liquid to the canisters is disadvantageous because there can be different flow rates to each canister when such peristaltic pumps are utilized. Further, the types of peristaltic pumps required are expensive. The use of a vacuum pump to draw the liquid into the canisters is also disadvantageous because if one of the tubes becomes occluded, all of the liquid will be rapidly drawn into only one of the canisters. Still further, the system of U.S. Pat. No. 4,036,698 has not been suggested for use with a plurality of samples.

It is an object of the present invention to provide a system for testing sterility that is inexpensive yet simple and efficient to operate.

Another object of the present invention is to provide a sterility testing system in which the sterility does not have to be broken during testing.

A further object of the further invention is to provide a sterility testing system which operates to reduce the occurrence of false positive results caused by extraneous contamination.

A still further object of the present invention is to provide a sterility testing system in which a plurality of samples may be tested for sterility simultaneously.

Other objects and advantages of the present invention will become apparent as the description proceeds.

BRIEF DESCRIPTION OF THE INVENTION

In accordance with the present invention, a system for testing sterility is provided. The system comprises a first conduit for connection at its upstream end to a sample to be tested, and second and third conduits for connection to the downstream end of the first conduit. The second and third conduits are dimensioned to permit equal liquid flow therethrough.

A first discrete test chamber is provided for connection to the downstream end of the second conduit, and a second discrete test chamber is provided for connection to the downstream end of the third conduit. The first and second test chambers each include a main chamber portion and a filter located downstream of the main chamber portion. An inlet communicates with the main chamber portion for connection to the downstream end of the respective second or third conduits and a test media inlet communicates with the main chamber portion for enabling introduction of test media into the main chamber. An air vent communicates with the main chamber portion for enabling gravity flow of the liquid to be tested into the main chamber portion.

In the illustrative embodiment, means are provided downstream of the filter for connection to a vacuum pump, whereby the liquid that has been gravity fed to the chamber is pumped through the filter. In the illustrative embodiment, a plurality of conduits are connected to the upstream end of the first conduit, and each of the plurality of conduits is connected at its upstream end to a different sample to be tested.

In the illustrative embodiment, the test media inlet comprises an injection site and the first conduit comprises a first disposable flexible plastic tube, the second and third conduits comprise second and third equal sized disposable flexible plastic tubes, and the first and second test chambers each comprise equal sized plastic cylinders.

A more detailed explanation of the invention is provided in the following description and claims, and is illustrated in the accompanying drawings.

BRIEF DESCRIPTION OF THE DRAWINGS

FIG. 3 is a cross-sectional elevation of the bottom cap and membrane filter of the test chamber of FIGS. 1 and 2, and is taken along the plane of the line 3—3 of FIG. 5;

FIG. 4 is a fragmentary enlarged view of a portion of FIG. 3;

FIG. 5 is a top view, with a portion of the membrane broken away for clarity, of the bottom cap and membrane of a test chamber; and FIG. 6 is a bottom view of the bottom cap.

DETAILED DESCRIPTION OF THE ILLUSTRATIVE EMBODIMENT

Figure 1:
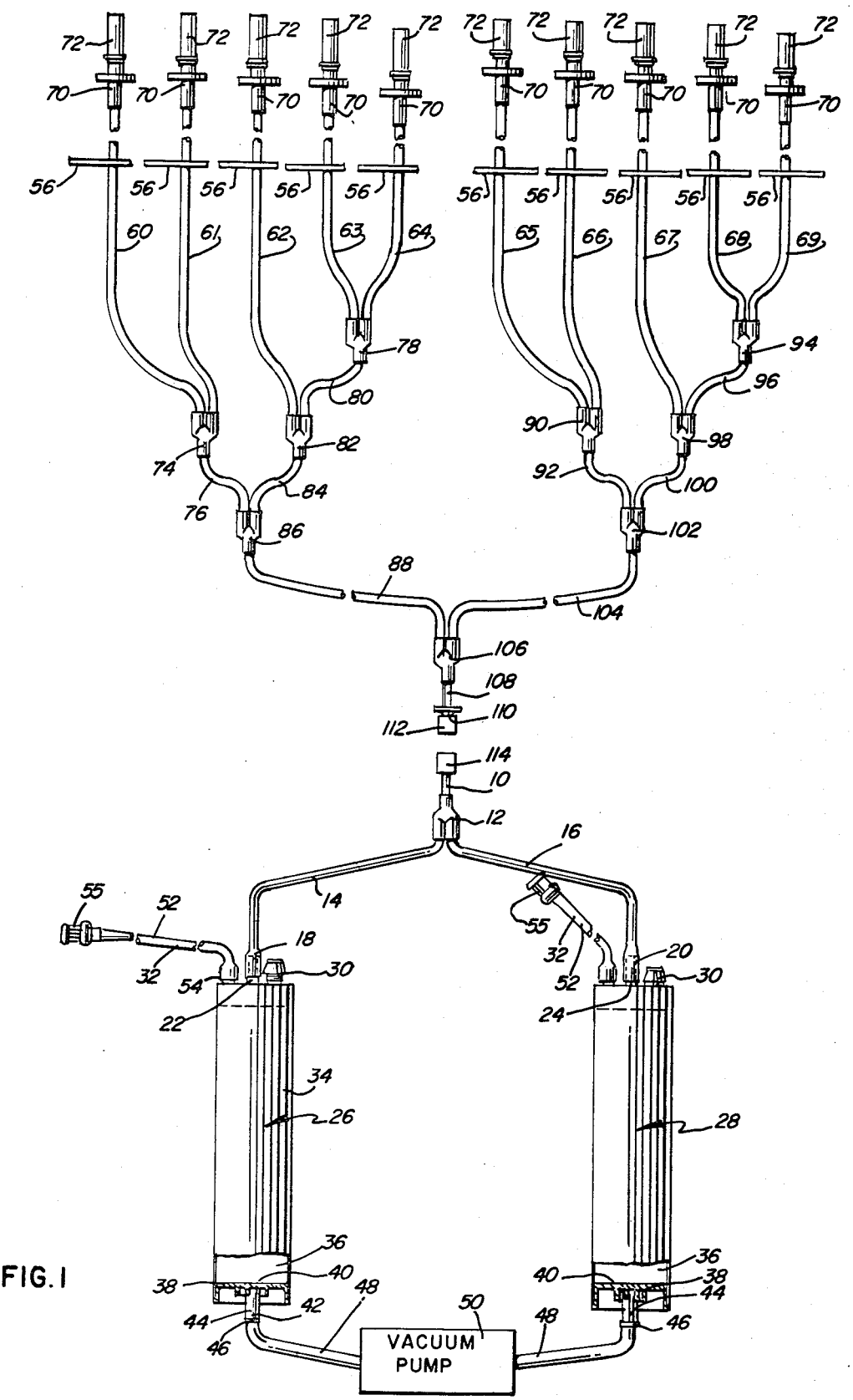
FIG. 1 is a view of a system for testing the sterility of a plurality of samples, in accordance with the principles of the present invention.
Figure 2:
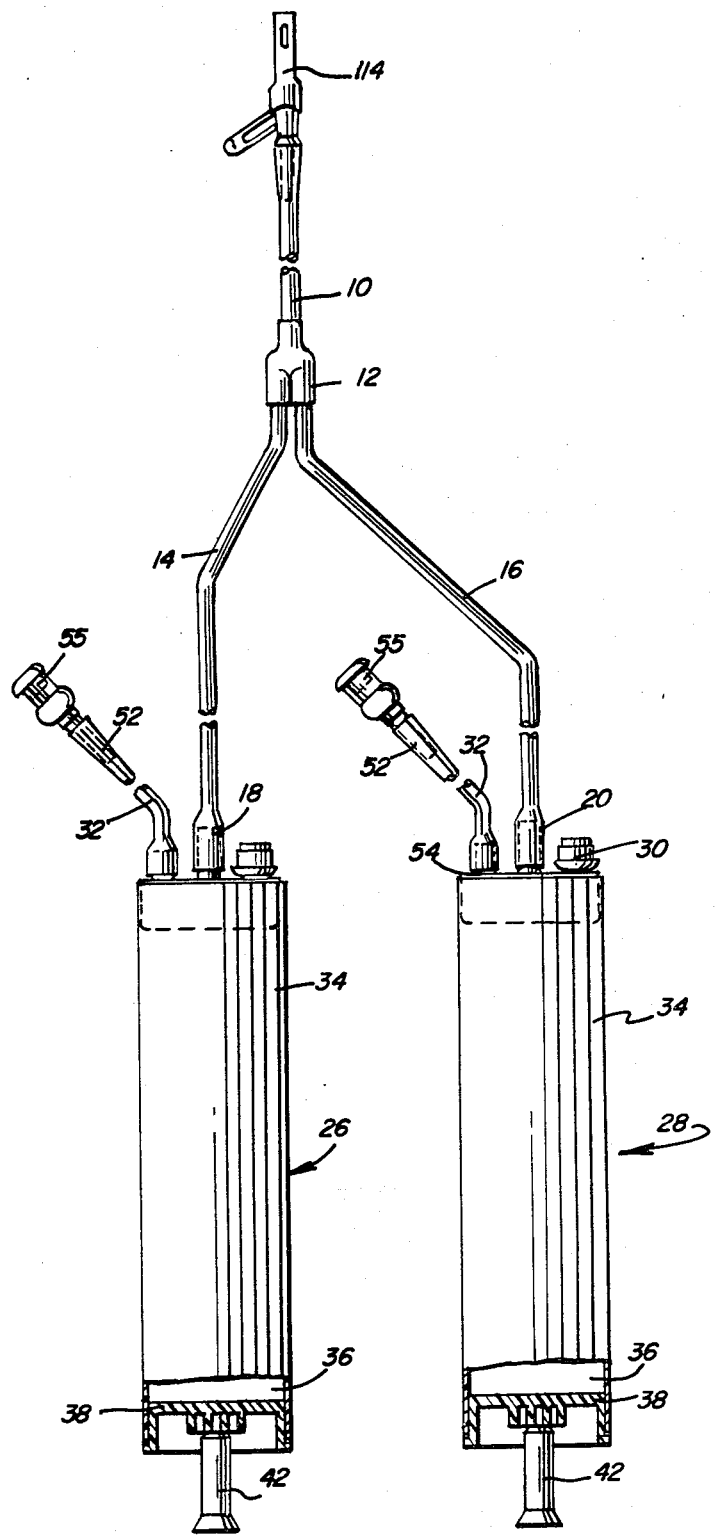
FIG. 2 is an enlarged view of a portion of the system of FIG. 1, including the first, second and third conduits and first and second test chambers.

Referring to the drawings, and to FIGS. 1 and 2 in particular, the sample to be tested is fed to a first conduit 10 which is coupled by means of an inverted Y junction 12 to second conduit 14 and third conduit 16. Each of conduits 10, 14 and 16 is preferably formed of flexible plastic tubing, with conduits 14 and 16 being equal in size. Conduits 10, 14 and 16 may comprise continuous, integral plastic tubing and conduits 14 and 16 are dimensioned to permit equal liquid flow therethrough. The downstream ends 18 and 20 of conduits 14 and 16, respectively, are connected to inlets 22 and 24, respectively, of first test chamber 26 and second test chamber 28, respectively. Test chambers 26 and 28 are identical to each other and each comprises a test media inlet 30 and an air vent 32. Each of the test chambers 26 and 28 includes a rigid vinyl cylindrical body portion 34 which defines a main chamber portion 36 and encloses a bottom cap 38 at its downstream end, which bottom cap 38 supports a membrane filter 40 thereon. Cylindrical body 34 of the test chamber is formed of a rigid polymer which has sufficient wall thickness to prevent oxygen diffusion in quantities that would disrupt the test. It is preferred that the body of the test chamber be formed of PVC having a thickness of at least 0.020 inch.

The bottom cap 38, which is described in more detail below, has an extending tip 42, the bore 44 of which communicates with filter 40 and the distal end 46 of which is coupled via tubing 48 to a vacuum pump 50.

Test media inlet 30 comprises an injection site for injecting into main chamber 36 suitable microorganism growth media. Although injection site 30 is shown as fastened to chamber 36 the injection site could be connected into conduit 14, using a Y-site or the like, so long as the injection site is in communication with main chamber portion 36.

Air vent 32 is filtered by a bacteriological retentive and hydrophobic filter. The air vent 32 comprises tubing 52 coupled at one end to inlet 54 of the test chamber and at its other end to an air filter 55.

In one embodiment of the present invention, a number of samples, such as ten samples, are simultaneously tested for sterility. To this end, ten purportedly sterilized bottles of solution are taken at random from a production line or the like, and each of the bottles is connected to one of conduits 60–69 (FIG. 1). An on-off slide clamp 56 is coupled to each of conduits 60–69, so that flow to the lines is prevented until all the lines are properly coupled.

Conduits 60–69 are formed of flexible plastic tubing, a connector portion 70 is provided at the upstream end at each of conduits 60–69, with the connector portion 70 including a piercing tip and having a tip protector 72 thereon, with some of the tip protectors carrying a cotton assembly. The piercing tips are inserted into the female receptacle portions of the sterile bottle assembly containing the sample to be tested. The downstream ends of conduits 60 and 61 are connected through an inverted Y junction 74 to a conduit 76. The downstream ends of conduits 63 and 64 are connected through an inverted Y junction 78 to conduit 80 and the downstream ends of conduits 62 and 80 are connected through inverted Y junction 82 to conduit 84. Conduits 76 and 84 are connected through inverted Y junction 86 to conduit 88.

Conduits 65 and 66 are connected through inverted Y junction 90 to conduit 92. The downstream ends of conduits 68 and 69 are connected through an inverted Y junction 94 to conduit 96. The downstream ends of conduits 67 and 96 are connected through inverted Y junction 98 to conduit 100. The downstream ends of conduits 92 and 100 are connected through inverted Y junction 102 to conduit 104. The downstream ends of conduits 88 and 104 are connected through inverted Y junction 106 to a single tube 108 having a male end connector 110 that is covered by tip protector 112. A female receptacle at the upstream end of first conduit 10 is covered by a tip protector 114. Tip protectors 112 and 114 are removed and conduits 108 and 10 are connected together so that all 10 conduits 60–69 will effectively feed via inverted Y junctions and other tubing to first conduit 10.

The bottom cap 38 is shown in greatest detail in FIGS. 3–6. Referring to these Figures, it is seen that the bottom cap 38 comprises a unitary molded unit having a top portion 116 with three concentric rings 42, 118 and 120 extending downwardly therefrom. Ring 42 defines bore 44 and comprises the outlet of the test chamber, with bore 44 communicating with membrane 40 through a passage 121 and a generally conical-shaped opening 122. Ring 120 comprises the outer wall of the bottom cap 38.

As shown most clearly in FIGS. 4 and 5, the top surface of top portion 116 comprises a number of radially extending ribs 124 and 126, with ribs 124 extending substantially from the center of top portion 116 and with ribs 126 extending from about one-half the radius of the top portion 116, as illustrated in FIG. 5. Filter 40 is a membrane filter of suitable size to strain microorganisms from the liquid solution so that such microorganisms will be concentrated on the filter 40. Although no limitation is intended, an example of a suitable size microporous membrane filter is a 0.45 micron filter. Filter 40 is preferably sonic welded about its periphery to top portion 116, and ribs 124, 126 serve to prevent the filter from being totally sucked against the planar surface portion of top portion 116 during operation of vacuum pump 50.

In the operation of the present invention, all of the tubing is appropriately connected and a number of sample sterilized bottles of solution are taken at random and connected to conduits 60–69. The sterilized solution bottles are maintained at a predetermined height with respect to test chambers 26 and 28, so that there will be a satisfactory head for proper gravity flow of the liquid to the test chambers. Although no limitation is intended, a three-foot head has been found satisfactory to obtain a flow rate of about 10 liters per 30 minutes. Since the main chambers 36 of test chambers 26 and 28 are open to the atmosphere via air vents 32, the liquid is fed by gravity into the main chambers 36, avoiding the need for using peristaltic pumps or vacuum systems to draw the liquid into the main chamber. In this manner, a simple and efficient system is provided which enables gravity flow of the liquids into the two test chambers.

The tubing is connected together in the appropriate manner, as illustrated in FIG. 1, and slide clamps 56 are moved to their open position, so that the liquid will flow by gravity through the conduits and into chambers 36. The liquid is drawn through the filters 40 by means of vacuum pump 50 so that the microorganisms will be strained from the liquid and will be deposited upon the filters. It is preferred that the pull of vacuum pump 50 be substantially equal to the gravity flow rate of the liquid into chambers 36.

After the liquid has been removed from chambers 36 and the microorganisms are concentrated upon filters 40, chambers 26 and 28 are sealed and test media are injected into injection sites 30. Different test media are injected into each of the test chambers, and the test chambers are placed in an incubator for a predetermined period of time.

By using the present invention, there is no need to remove the filter or to cut the filter, the need for peristaltic pumps or a vacuum pumping system to draw the solution into the test chamber is obviated and a number of samples may be tested simultaneously if desired.

Although an illustrative embodiment of the invention has been shown and described, it is to be understood that various modifications and substitutions may be made by those skilled in the art without departing from the novel spirit and scope of the present invention.

What is claimed is:

1. A method for testing sterility, which comprises the steps of:

connecting a conduit at its upstream end to a sample to be tested;

gravity-feeding the sample to be tested without vacuum through the conduit and to a test chamber connected to the downstream end of the conduit, said test chamber including a main chamber portion and a filter located downstream of said main chamber portion, an inlet communicating with the main chamber portion for connection to the downstream end of the conduit, a separate test medium inlet communicating with the main chamber portion for enabling introduction of a test medium into the main chamber portion without requiring disconnection of the downstream end of the conduit from said inlet, and an air vent communicating with the main chamber portion for venting the main chamber portion during flow of the sample to be tested into the main chamber portion, whereby the sample to be tested may be fed into the main chamber portion by gravity flow;

drawing the sample to be tested through said filter within the main chamber portion using a vacuum pump;

injecting a test medium to the test chamber through said test medium inlet;

incubating the test chamber; and observing the filter.

2. A method for testing sterility as described in claim 1, in which a plurality of samples are fed to the conduit.

3. A method for testing sterility as described in claim 1, wherein the gravity flow to the test chamber is substantially equal to the pull of the sample through the filter.

* * * * *